United States Patent
Newman et al.

(10) Patent No.: US 11,241,477 B2
(45) Date of Patent: Feb. 8, 2022

(54) OXYTOCIN COMPOSITIONS FOR TREATMENT OF TINNITUS

(71) Applicant: New York University, New York, NY (US)

(72) Inventors: Lawrence C. Newman, Katonah, NY (US); James Cramer, Summit, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/007,518

(22) Filed: Aug. 31, 2020

(65) Prior Publication Data

US 2021/0060119 A1  Mar. 4, 2021

Related U.S. Application Data

(60) Provisional application No. 62/893,363, filed on Aug. 29, 2019.

(51) Int. Cl.
*A61K 38/095* (2019.01)
*A61P 27/16* (2006.01)
*A61K 9/00* (2006.01)

(52) U.S. Cl.
CPC .......... *A61K 38/095* (2019.01); *A61K 9/0043* (2013.01); *A61P 27/16* (2018.01)

(58) Field of Classification Search
None
See application file for complete search history.

(56) References Cited

U.S. PATENT DOCUMENTS

| 8,198,240 | B2* | 6/2012 | Yeomans | A61K 9/0043 514/11.6 |
|---|---|---|---|---|
| 2010/0311655 | A1 | 12/2010 | Leonard et al. | |
| 2013/0085106 | A1 | 4/2013 | Pedersen et al. | |
| 2016/0193282 | A1 | 7/2016 | Yeomans et al. | |
| 2016/0310683 | A1 | 10/2016 | Djupesland et al. | |
| 2020/0376000 | A1* | 12/2020 | Tkachenko | A61P 15/00 |

FOREIGN PATENT DOCUMENTS

WO  2011140608 A1  11/2011

OTHER PUBLICATIONS

Azevedo et al., Tinnitus Treatment with Oxytocin: A Pilot Study, Sep. 2017, Frontiers in Neurology, vol. 8 Article 494, pp. 1-7. (Year: 2017).*

* cited by examiner

*Primary Examiner* — Nannette Holloman
(74) *Attorney, Agent, or Firm* — Hodgson Russ LLP

(57) ABSTRACT

Provided are methods and compositions for treatment of tinnitus. The method comprises administration of therapeutically effective amount of oxytocin, which may be present with a thickener, and may be delivered to the back of the nasal cavity in a suitable form. Compositions of oxytocin for intranasal delivery and sprayable unit compositions of oxytocin are also provided.

20 Claims, No Drawings

Specification includes a Sequence Listing.

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5
```

OXYTOCIN COMPOSITIONS FOR TREATMENT OF TINNITUS

CROSS-REFERENCE TO RELATED APPLICATION

This application claims priority to U.S. Provisional patent application No. 62/893,363, filed on Aug. 29, 2019, the disclosure of which is incorporated herein by reference.

BACKGROUND OF THE INVENTION

Tinnitus is the perception of noise or ringing in the ears. Tinnitus is typically subjectively perceptual, which means that only the affected subject can perceive the sound. The perceived sensation may include ringing, roaring, static, buzzing, hissing, and whistling, in one or both ears. The noise may be intermittent or continuous. It is estimated that about 15% to 20% of people have experienced some degree of tinnitus. Severe or prolonged tinnitus can affect quality of life for the patient as well as their families. Tinnitus can lead to depression and anxiety problems. Current therapies include masking, sound therapy, electrical stimulation, and chemical therapeutics. However, these treatments do not provide satisfactory relief and therefore, there continues to be a need to develop more effective therapies.

SUMMARY OF THE DISCLOSURE

This disclosure provides compositions and methods for treatment of tinnitus. The compositions comprise therapeutically effective doses of oxytocin suitable for intranasal administration. The oxytocin may be in an inhalable, sprayable or powdered form suitable for administration into the nasal passage or nasal cavity. The compositions may comprise a thickener, which may be present in an amount of 4 to 12% by weight of the composition. The amount of oxytocin may be 100 to 600 IU per ml of the composition. In an embodiment, the amount of oxytocin per dose may be 15 to 65 IU. A unit dose may be from 0.05 to 0.15 mls.

This disclosure also provides methods for treatment of tinnitus. In an aspect, the method comprises administering to an individual who is afflicted with tinnitus, one or more doses of oxytocin such that the tinnitus symptoms are reduced. A dose of oxytocin may be from 15 to 65 IU. In an embodiment, about 20 to 260 IU over a period of 24 hours in multiple doses may be administered.

DESCRIPTION OF THE DISCLOSURE

The present disclosure provides compositions and methods for treatment of tinnitus. The compositions comprise therapeutically effective doses of oxytocin for intranasal administration. The methods comprise administering intranasally to an individual in need of treatment a composition comprising a therapeutically effective amount of oxytocin. A therapeutically effective amount may be delivered in one or more doses.

Oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO:1). The oxytocin peptide for use in the present methods can be natural or synthetic, or may be produced by recombinant technologies. Oxytocin is also commercially available. Peptide analogs and derivatives of oxytocin are known in the art and can be used in the present methods.

Some example of oxytocin analogs include 4-threonine-1-hydroxy-deaminooxytocin, 4-serine, 8-isoleucine-oxytocin, 9-deamidooxytocin, 7-D-proline-oxytocin and its deamino analog, (2,4-diisoleucine)-oxytocin, deamino oxytocin analog, 1-deamino-1-monocarba-E12-Tyr(OMe)]-OT(dCO-MOT), carbetocin, 4-threonine, 7-glycine-oxytocin (TG-OT), oxypressin, deamino-6-carba-oxytoxin (dC60), L-371, 257 and the related series of compounds containing an ortho-trigluoro-ethoxyphenylacetyl core such as L-374,943. Additional examples of oxytocin analogs can be found in U.S. Patent Application Publication 2014/0066373 to Cai (the description of which analogs is incorporated herein by reference). Oxytocin or analogs may be chemically modified, for example, by amidation, the use of D amino acids in the peptide, incorporation of small non-peptidyl moieties, as well as the modification of the amino acids themselves (e.g., alkylation or esterification of side chain R-groups). Such analogs, derivatives and fragments should at least substantially retain the desired biological activity of the native oxytocin peptide of SEQ ID NO:1. For example, in embodiments, such analogs may retain at least 70%, at least 80%, at least 90%, or at least 95% of the activity of oxytocin of SEQ ID NO:1.

The term "treatment" as used herein refers to reduction in one or more symptoms or features associated with the presence of the particular condition being treated. Treatment does not necessarily mean complete cure or remission, nor does it preclude recurrence or relapses. For example, treatment in the present disclosure means reducing one or more symptoms associated with tinnitus. Treatment can be orientated symptomatically, for example, to suppress symptoms. It can be effected over a short period, over a medium term, or can be a long-term treatment, such as, for example, within the context of a maintenance therapy. Administrations may be intermittent, periodic, or continuous.

The term "therapeutically effective amount" as used herein in reference to a single agent is the amount sufficient to achieve, in a single or multiple doses, the intended purpose of treatment. The exact amount desired or required will vary depending on the particular compound or composition used, its mode of administration, patient specifics, and the like. Appropriate effective amounts can be determined by one of ordinary skill in the art informed by the present disclosure.

Where a range of values is provided in this disclosure, it should be understood each intervening value to the tenth of the value of the lower limit, and all intervening ranges between the upper and lower limit of that range are encompassed within the invention, unless clearly indicated otherwise.

A reference to singular form also includes its plural form, and vice versa.

The present compositions may be delivered intranasally. The term "intranasal delivery" as used herein means the composition or active agent (oxytocin) is delivered to the nose, nasal passageways or nasal cavity. The oxytocin or compositions comprising oxytocin may be in the form of spray, drops, powder, suspension, gel, inhalant, aerosolized, or any other suitable form.

Compositions comprising oxytocin can be prepared for pharmaceutical use by incorporation with a pharmaceutically acceptable carrier or diluent. The compositions can be formulated for intranasal delivery. The formulations may comprise excipients, vehicles, emulsifiers, stabilizers, preservatives, mucosal adhesives, antibacterial agents, buffers, and/or other additives. General pharmaceutical formulation components and methods of preparation can be found in Remington's Pharmaceutical Sciences, 2000, 20th ed.

In an embodiment, oxytocin formulations for the present methods may be in the form of powder (such as a dry powder), liquid based, or aerosolized. When used in a powder form, the powder may be substantially pure oxytocin (such as at least 50%, 60%, 70%, 80%, 90%, 95%, or 99%), or may contain other components such as salts, and the like. In an embodiment, the powder may be 94-99% pure oxytocin. When used in a liquid based or aerosolized form, the composition may contain salts and buffers, and may optionally contain a thickener. The compositions may also optionally contain excipients, carriers, and the like. Oxytocin may be present as incorporated in nanoparticles, including liposomes.

In an embodiment, the oxytocin formulations may be liquid based or aerosolized and comprise a magnesium salt, such as, magnesium chloride or magnesium citrate, and the like.

In an embodiment, oxytocin is present as a sprayable composition. The sprayable composition (which may also be delivered as drops or aerosolized) may comprise or consist essentially of oxytocin and salts. In an embodiment, the composition comprises, consists essentially of, or consists of oxytocin, magnesium salt, sodium citrate, and citric acid. In an embodiment, the composition further comprises a mucoadhesive polymer. The sprayable compositions may be delivered using a sprayer. The sprayer may include an operating mechanism (a spray head or a pump) in fluid communication with a reservoir. The spray device may be manually actuated or may be pressurized.

The amount of oxytocin may be 100 to 600 IU per ml of the composition. In an embodiment, the amount of oxytocin per ml can be 150 to 450 IU. In various embodiments, the oxytocin can be 150, 200, 250, 300, 350, 400, or 450 IU per ml.

The magnesium salt may be any pharmaceutically acceptable magnesium salt. Examples include magnesium chloride, magnesium citrate, magnesium acetate, and the like.

A "mucoadhesive agent" (also referred to herein as a "thickener") generally refers to compounds that adhere to the mucosal surface. Mucoadhesive agents may be polymers such as anionic polymers (such as alginate, xanthan gum, carageenan), cationic polymers (such as, chitosan), non-ionic polymers (such as guar gum), amphoteric polymers, synthetic polymers, and the like. In an embodiment, the mucoadhesive polymer is Mucolox™. These agents generally increase the viscosity of the composition. In an embodiment, a mucoadhesive agent may have a viscosity of from 4,000 to 12,000 cps. In an embodiment, the mucoadhesive agent has a viscosity of from 5,000 to 10,000 cps. In various embodiments, the viscosity of the mucoadhesive agent may be 5,000, 6,000, 7,000, 8,000, 9,000, 10,000, 11,000 cps.

In an embodiment, the present composition is present in a sprayable unit dose for intranasal administration comprising or consisting essentially of from 15 to 65 IU of oxytocin per unit dose. In an embodiment, the present composition is present in a sprayable unit dose for intranasal administration comprising or consisting essentially of from 15 to 65 IU of oxytocin per unit dose and a thickener present in an amount of from about 5% to 12% by weight of the composition, wherein the thickener has a viscosity of from about 4,000 to 12,000 cps. In an embodiment, the unit dose may comprise 20, 25, 30, 35, 40, 45, 50, 55, or 60 IU of oxytocin. The unit dose may be from 0.05 to 0.15 mls. In embodiments, the unit dose may be 0.05, 0.06, 0.07, 0.08, 0.09, 0.1, 0.11, 0.12, 0.13, 0.14, or 0.15 mls. In an embodiment, the unit dose is about 0.1 ml.

In an embodiment, the disclosure provides a pharmaceutical composition for intranasal administration comprising or consisting essentially of: a) from 100 to 600 IU of oxytocin per ml, optionally, b) a thickener present in an amount of from 5% to 12% by weight of the composition, wherein the thickener has a viscosity of from about 4,000 to 12,000 cps; and optionally, c) magnesium chloride, citric acid and sodium citrate.

In an embodiment, this disclosure provides a pharmaceutical composition suitable for intranasal administration comprising oxytocin, and a thickener (viscosity regulating agent) present in an amount of from about 1% to about 15% by weight of the composition. The thickener, such as Mucolox™ may be present in an amount of from 5% to 12% (having a viscosity of 4,000 to 12,000 cps). The oxytocin may be present in an amount of 0.05 to 0.1% by weight. The oxytocin may be from 100 to 600 IU per ml. The composition may comprise salts, such as magnesium salts, zinc salts, sodium salts, and the like, and buffers. In an embodiment, the composition may comprise oxytocin present in an amount of 0.05% to 0.1% by weight; a thickener in an amount of about 5% to 12% by weight, said thickener having a viscosity of about 4,000 to 12,000 cps, one or more salts or buffers.

In an embodiment, the oxytocin is present in a powdered form. In the powdered formulation, oxytocin may be delivered as the only component, or other components may be mixed with the powder, such as magnesium or zinc salts, and the like. Dry powder forms of oxytocin are known in the art (See, for example, Fabio et al., AAPS PharmSciTech, vol. 16, no. 6, 1299-1306, 2015, incorporated herein by reference). For example, oxytocin powders preparations for inhalation may contain excipients and stabilizing agents, such as trehalose, isoleucine, polyvinyl-pyrrolidone, citrate (sodium citrate and citric acid), and zinc salts (such as zinc chloride and zinc citrate).

In an embodiment, a nasal spray formulation can be made as follows: for a total quantity of 38.0 mls, oxytocin powder was 0.3080 gm, magnesium chloride was 2.3 gm, citric acid anhydrous granular was 0.1080 gm, sodium citrate powder was 2.15 gm, PCCA Mucolox liquid was 3.8 mls, and remaining was water (formulation 1). This provides 45 IU units of oxytocin per 0.1 ml of the nasal spray. In another embodiment, the formulation can be made as follows: for a total quantity of 30.0 mls, oxytocin 10 units/mg trituration was 0.0.45 gm, magnesium chloride crystals was 1.83 gm, citric acid anhydrous granular was 0.0860 gm, sodium citrate powder was 1.7 gm, PCCA Mucolox liquid was 3.0 mls, and remaining was water (formulation 2). This provides 15 units IU units of oxytocin per 0.1 ml of the nasal spray.

In an aspect, this disclosure provides a method for treating tinnitus. The method comprises administering intranasally to an individual a composition comprising or consisting essentially of oxytocin, wherein such administration results in treatment of tinnitus. The effectiveness of treatment of tinnitus may be monitored by quantifying tinnitus, such as by self-evaluation using clinically accepted techniques. An example is the Tinnitus Handicap Inventory ("THI"), a validated and published measurement technique. (Newman et al., Arch Otolaryngol Head Neck Surg, 1996, February 122(2), 143-8). In an embodiment, the improvement in an individual using THI may comprise an improvement of at least 10%. In various embodiments, the improvement may comprise from 10-100%, such as at least 20, 30, 40, 50, 60, 70, 80, 90, 95, or 99%.

In an embodiment, the method comprises administering about 50 to 260 IU of oxytocin over a 24 hour period. In an embodiment, the method comprises delivering about 100 to 250 IU, 160-240 IU, or 50 to 200 IU over a 24 hour period. In various embodiments, the oxytocin delivered may be 50, 75, 100, 125, 150, 175, 200, 225, and 250 IU over a 24 hour period. The oxytocin amount over a 24 hour period may be delivered in 2-5 doses. In an embodiment, the doses may be from 1 to 6 or 2 to 6 or more. In an embodiment, it is delivered in 3, 4, or 5 doses. Each dose may deliver the same or different amount of oxytocin as the other doses. In an embodiment, each dose may deliver from 12 to 65 IU per dose.

The results of the present disclosure were unexpected because using lower amounts of oxytocin (such as under 20 IU per day) did not result in any significant relief. The addition of a mucoadhesive polymer results in having to use fewer doses per day and reduces the flow-out of the sprayed composition.

The present compositions may be delivered to any part of the nasal cavity. In an embodiment, the compositions may be delivered to the vascular rich upper nasal cavity. For example, devices may be used that specifically deliver compositions to the upper nasal cavity. This enables active agents to rapidly enter the circulation, and particularly the central nervous system. Devices developed for delivery to the upper nasal cavity include those described in U.S. Pat. Nos. 9,550,036 and 9,919,117 (incorporated herein by reference) to Impel Neuropharma Inc. The compositions delivered using these devices may be liquid-based or may be in a dry powdered form. In an embodiment where the compositions are delivered to the upper nasal cavity, the mucoadhesive polymer may not be necessary. In an embodiment, a composition comprising or consisting essentially of oxytocin and optionally salts and/or buffer, and containing no thickener may be delivered to the upper nasal cavity. The amount of oxytocin delivered to the upper nasal cavity over a 24 hour period may be less than what is required if delivered as to the outer nasal cavity. For example, the oxytocin delivered to the upper nasal cavity may be from 50 to 260 IU or 50 to 200 IU of oxytocin over a 24 hour period or may be less than 50 IU, such as, for example, 20 to 200 or 20 to 50 IU over a 24 hour period. In embodiments, the oxytocin delivered may be 20 to 260 IU, 50 to 250 IU, 50 to 225 IU, 100 to 225, 20 to 225 IU, and all values and ranges between 20 and 260 IU over a 24 hour period.

Individuals that can be treated with the present compositions include those who are suffering from tinnitus. While the present method is useful for those individuals who are afflicted with tinnitus but do not suffer from migraine, the method can also be used for those individuals in whom tinnitus is accompanied by migraine. The present compositions are useful for treatment of tinnitus in male subjects, and non-pregnant female subjects.

The following are some non-restrictive examples of the embodiments of this disclosure.

Example 1. A method of treating tinnitus comprising administering intranasally to an individual in need of treatment from 50 to 260 IU of oxytocin over a 24 hour period.

Example 1a. The method of Example 1, wherein the individual is administered from 50 to 250, 50 to 225, 50 to 200, 100 to 225, 100 to 250, or 100 to 200 IU of oxytocin over a 24 hour period.

Example 1b. The method of Example 1a, wherein the individual is administered from 100 to 200 IU or 100 to 225 of oxytocin over the 24 hours period.

Example 1c. The method of Example 1b, wherein the individual is administered from 160 to 200 IU of oxytocin over the 24 hour period.

Example 1c.1 The method of Example 1c, wherein the individual is administered about 180 IU of oxytocin over the 24 hour period.

Example 1d. The method of any of the preceding Examples, wherein the oxytocin is delivered in 3, 4, or 5 doses over the 24 hour period.

Example 1e. The method of Example 1d, wherein each dose delivers from about 12 to 65 IU of oxytocin.

Example 1f. The method of Example 1, wherein oxytocin is delivered in a composition which further comprises a thickener present in an amount of from 5% to 12% by weight of the composition, said thickener having a viscosity of from 4,000 to 12,000 cps.

Example 1g. The method of Example 1, wherein the administration is continued for days, weeks, or months.

Example 1h. The method of Example 1, wherein the individual is a male or a post-menopausal female.

Example 1i. The method of Example 1, wherein the individual is also suffering from migraine.

Example 1j. The method of Example 1, wherein the individual is not suffering from migraine.

Example 2. A sprayable composition for intranasal administration comprising about 100 to 600 IU of oxytocin per ml, and a thickener present in an amount of from 5% to 12% by weight of the composition, said thickener having a viscosity of from about 4,000 to 12,000 cps.

Example 2a. The sprayable composition of Example 2, wherein the composition comprises about 150 to 450 IU of oxytocin per ml.

Example 2b. The sprayable composition of Example 2, wherein the thickener is Mucolox™.

Example 2c. The sprayable composition of Example 2 further comprising salts and/or buffers.

Example 3. A sprayable unit dose of oxytocin formulated for intranasal administration comprising from 15 to 65 IU of oxytocin and a thickener present in an amount of from about 5% to 12% by weight of the composition, said thickener having a viscosity of from about 4,000 to 12,000 cps.

Example 3a. The sprayable unit dose of Example 3, wherein the volume of the dose is about 0.05 to 0.15 ml, such as 0.1 ml.

Example 3b. The sprayable unit dose of Example 3, wherein the thickener is Mucolox™.

Example 4. A pharmaceutical composition suitable for intranasal administration comprising oxytocin, and a viscosity regulating agent present in an amount of from about 1% to about 15% by weight of the composition.

Example 4a. The pharmaceutical composition of Example 4, wherein the viscosity regulating agent is Mucolox™ present in an amount of from 5% to 12%.

Example 4b. The pharmaceutical composition of Example 4 or 4a, wherein oxytocin is present in an amount of 0.05 to 0.1% by weight.

Example 4c. The pharmaceutical composition of any of Example 4-4b, further comprising salts and/or buffers.

Example 4d. The pharmaceutical composition of any of Example 4-4b, further comprising magnesium chloride, citric acid, and sodium citrate.

Example 5. A pharmaceutical composition for intranasal administration comprising or consisting essentially of:

a) oxytocin present in an amount of 0.05 to 0.1% by weight;

b) a thickener in an amount of about 5% to 12% by weight, said thickener having a viscosity of about 4,000 to 12,000 cps, and c) one or more salts or buffers.

Example 5a. The pharmaceutic composition of Example 5, wherein the salts or buffers are magnesium chloride, sodium citrate, and citric acid.

Example 6. A pharmaceutical composition for intranasal administration comprising or consisting essentially of:

a) from 100 to 600 IU of oxytocin per ml, b) a thickener present in an amount of from 5% to 12% by weight of the composition, said thickener having a viscosity of from about 4,000 to 12,000 cps, and c) magnesium chloride, citric acid, and sodium citrate.

Example 7. A method of treating tinnitus in an individual comprising delivering to the upper nasal cavity of the individual oxytocin in a powdered or aerosolized form.

Example 7a. The method of Example 7, wherein the oxytocin is delivered in a powdered form at an amount of about 20 to 200 IU of oxytocin over a 24 hour period.

Example 7b. The method of Example 7a, wherein the oxytocin powder is at least 95% pure oxytocin.

Example 8. A method of treating tinnitus in an individual comprising delivering to the upper nasal cavity of the individual oxytocin present in a sprayable composition, in one or more doses, from 20 to 260, 20 to 225, or 20 to 200 IU of oxytocin over a 24 hour period.

Example 8a. The method of Example 8, wherein delivery is achieved by propelling the composition into the upper nasal cavity.

Example 8b. The method of Example 8, wherein the oxytocin composition contains a mucoadhesive polymer.

Example 9. Compositions for use in any of the methods from any of the preceding examples.

The following example is provided to further illustrative the invention and is not intended to be restrictive in any way.

Example

This example describes clinical use of the present formulations to treat tinnitus. In a patient suffering for tinnitus an initial dose of less than 20 IU daily was tried, but this did not provide any relief A compounded formulation of oxytocin that provided a dose of 60 IU daily (30 IU twice daily) was then used. The formulation contained oxytocin, magnesium chloride, citric acid, and sodium citrate in sterile water. The patient reported partial benefit. The dose was then increased to 45 IU (3 sprays of 15 IU) 4 times daily. This produced a significant relief. A thickener was then added to the formulation keeping the oxytocin amount the same. The patient then reported several days of tinnitus free period. His score on the Tinnitus Handicap Inventory reduced from a pretreatment score of 96 (meaning a catastrophic level) to a current score of 14 (meaning mild or no tinnitus). The patient has remained improved over 1 year since initiating therapy. His current dose is 22.5 IU in each nostril 4 times daily. Since his tinnitus occurs in distinct cycles, at times when tinnitus severity is loudest, he increases the dose to 5 times daily for 2 days. Over the past 3 months, this dosage regimen has reduced tinnitus severity and has allowed him to go as long as 10 days without tinnitus. His current handicap inventory is 8.

In another patient with tinnitus, an oxytocin dose of 45 IU twice daily was found to be of significant benefit. This patient has reported that his tinnitus volume has reduced by 45-60% for the first time in several years and he also has some days in which he is tinnitus free. He remains improved on this dosing schedule for more than a year.

In another patient where tinnitus was caused by a drug, a dose of 30 IU twice daily was used without benefit. The dose was increased to 45 IU 4 times daily resulting in a decrease in tinnitus volume by approximately 30%.

In another patient, who developed constant tinnitus after a neck injury one year ago, a dose of 45 IU (22.5 IU in each nostril) 4 times daily was used for 30 days and is still ongoing. It has provided about 15% improvement. On occasions, the patient has raised the dose to 5 times daily resulting in diminished tinnitus volume.

In another patient with constant tinnitus a dose of 30 IU 4 times daily has been started and treatment is ongoing. After 2 weeks, he has noticed that for the first time in 3 years, he can go several hours per day without noticing the tinnitus. And that the tinnitus intensity has lowered.

While the present invention has been described through illustrative embodiments, routine modification will be apparent to those skilled in the art and such modifications are intended to be within the scope of this disclosure.

What is claimed is:

1. A method of treating tinnitus comprising administering intranasally to an individual in need of treatment from 50 to 260 IU of oxytocin over a 24 hour period.

2. The method of claim 1, wherein the individual is administered from 100 to 225 IU of oxytocin over the 24 hour period.

3. The method of claim 1, wherein the individual is administered from 160 to 200 IU of oxytocin over the 24 hour period.

4. The method of claim 1, wherein the oxytocin is delivered in 3 to 5 doses over the 24 hour period.

5. The method of claim 4, wherein each dose delivers from about 12 to 65 IU of oxytocin.

6. The method of claim 1, wherein oxytocin is delivered in a composition which further comprises a thickener present in an amount of from 5% to 12% by weight of the composition, said thickener having a viscosity of from 4,000 to 12,000 cps.

7. The method of claim 1, wherein the individual is also suffering from migraine.

8. The method of claim 1, wherein the oxytocin is in a powdered or aerosolized form and is delivered to the upper nasal cavity of the individual.

9. The method of claim 8, wherein the oxytocin powder is at least 95% pure oxytocin.

10. The method of claim 8, wherein delivery is achieved by propelling the composition into the upper nasal cavity.

11. A method of treating tinnitus in an individual comprising delivering to the upper nasal cavity of the individual oxytocin in a powdered or aerosolized form, wherein the oxytocin is delivered in a powdered form at an amount of about 20 to 225 IU of oxytocin over a 24 hour period.

12. The method of claim 11, wherein the oxytocin is in a powdered form and the powder is at least 95% pure oxytocin.

13. The method of claim 11, wherein delivery is achieved by propelling the composition into the upper nasal cavity.

14. The method of claim 11, wherein the oxytocin composition further comprises a mucoadhesive polymer.

15. A pharmaceutical composition for intranasal administration comprising about 100 to 600 IU of oxytocin per ml, and a thickener present in an amount of from 5% to 12% by weight of the composition, said thickener having a viscosity of from about 4,000 to 12,000 cps.

16. The pharmaceutical composition of claim 15, wherein the composition is sprayable.

17. The sprayable pharmaceutical composition of claim 16, wherein the composition comprises about 150 to 450 IU of oxytocin per ml.

18. A sprayable unit dose of oxytocin formulated for intranasal administration comprising from 15 to 65 IU of oxytocin and a thickener present in an amount of from about 5% to 12% by weight of the composition, said thickener having a viscosity of from about 4,000 to 12,000 cps.

19. The sprayable unit dose of claim 17, wherein the volume of the dose is from 0.05 to 0.15 ml.

20. The sprayable unit dose of claim 17, wherein the volume of the dose is 0.1 ml.

\* \* \* \* \*